United States Patent [19]
Koike et al.

[11] Patent Number: 5,928,250
[45] Date of Patent: Jul. 27, 1999

[54] CATHETER ASSEMBLY FOR INTRACARDIAC SUTURE

[75] Inventors: Kazuyuki Koike, Tokyo-to; Yoshikazu Kishigami; Katsuya Miyagawa, both of Osaka, all of Japan

[73] Assignee: Nissho Corporation, Osaka, Japan

[21] Appl. No.: 09/016,301

[22] Filed: Jan. 30, 1998

[30] Foreign Application Priority Data

Jan. 30, 1997 [JP] Japan .................................. 9-016300

[51] Int. Cl.⁶ .................................................. A61B 17/00
[52] U.S. Cl. .......................................................... 606/139
[58] Field of Search .................................. 606/139, 144, 606/148, 170, 171, 180, 232, 222, 223, 103, 96, 99, 1; 294/100; 128/898; 604/96, 164, 158

[56] References Cited

U.S. PATENT DOCUMENTS 4,582,056  4/1986  McCorkle, Jr. .
5,425,744  6/1995  Fagan et al. .

FOREIGN PATENT DOCUMENTS 0 362 113 A1  4/1990  European Pat. Off. .
0 769 272 A1  4/1997  European Pat. Off. .

*Primary Examiner*—Michael Buiz
*Assistant Examiner*—Vikki Trinh
*Attorney, Agent, or Firm*—Kubovcik & Kubovcik

[57] ABSTRACT

Disclosed is an assembly catheter for intracardiac suture. The assembly catheter includes a hooking catheter 3 provided with a suture-hooking means 32 at a distal end and with a manipulating element (grip) 33 at a proximal end; a piercing catheter 2 having lumen 21 for movably holding the hooking catheter 3 and provided with a piercing needle 25 at a distal end and with a hemostatic valve 24 as a hemostatic means at a proximal end, the distal portion 28 of the piercing catheter adjacent to the piercing needle 25 being easily bendable; a sheath 1 having a lumen 11 for movably holding the piercing catheter 2 and provided with a hemostatic valve 14 as a hemostatic means at a proximal end; and a catheter-bending means 4 connected to the piercing needle 25 of the piercing catheter 2; in which the distal portion 28 of the piercing catheter 2 can be bent by the catheter-bending means 4. The catheter assembly is applicable to intracardiac suture for various configurations of ASD.

12 Claims, 12 Drawing Sheets

CATHETER ASSEMBLY FOR INTRACARDIAC SUTURE

FIELD OF THE INVENTION

The present invention relates to a catheter assembly for an intracardiac suture and, more particularly, to a catheter assembly for an intracardiac suture procedure suitable for a surgical technique, a so-called transcatheter atrioseptopexy, in which a sewing device is inserted into a peripheral blood vessel and manipulated into the heart by cardiocatheterization under cross-sectional echocardiography to sew an atrial septal defect (ASD) by direct suturing.

BACKGROUND OF THE INVENTION

In general, congenital cardiac diseases such as ASD have been treated by a surgical operation. As a matter of course, such a surgical operation includes not only treatment of the affected part but also thoracotomy or laparotomy and causes significant damage to a patient. In particular, it causes serious damage to child patients who are poor in physical strength.

Recently, a non-operative method for occlusion of atrial septal defects has been developed, in which a cardiocatheter is transvascularly inserted into the heart. This method is known as a percutaneous transluminal therapeutic catheterization, and the first clinical success in this method was reported in 1976 by King and Mill. In the method of King et al, an atrial septal defect is closed by introducing a pair of umbrella-like members for the left atrium and the right atrium into the atria with an insertion tool composed of a double-layered catheter and a core wire coaxially arranged therein, placing the members on the opposite sides of the defect, and locking them together at a central hub which crosses the defect.

However, this method requires the use of a very large-sized insertion tool and hard umbrella-like members, thus making it impossible to apply it to children, especially to preschool children. For this reason, as a result of efforts to miniaturize such a device, Rashkind developed a single-umbrella type plug having a hook and succeeded in clinical application of the device to a child in 1977. However, this method has a defect that the plug is sometimes hooked on an unintended side of the heart because of being provided with the hook. Once the umbrella-like member is opened, it is impossible to change the hooked position as well as to draw back the device from the heart. This requires an emergency surgical operation when the plug is hooked on an unintended side of the heart. In order to overcome such disadvantages, Rashkind further developed a plug comprising two umbrella-shaped occluders having eight stainless steel struts and being connectable to each other. The device has been put into clinical use widely for occlusion of patient ductus arteriosus.

Japanese unexamined patent application No. 5-237128 filed by James E. Locket al. discloses an interatrial occlusion device comprising two umbrella-shaped members composed of eight stainless steel struts as in Rashkind's device, each strut being provided at a central part thereof with a spring coil. This device is firmly fixed to the thin interatrial septum by closely adhering the two umbrella-shaped members to each other in an overlapping state. This device is called a clam shell-shaped interatrial occluder because of its configuration similar to that of a clam being a bivalve. The procedure is carried out by inserting an elongated sheath with a thickness of 11 French through the femoral vein. This device has been widely used for closing atrial septal defects by means of percutaneous transluminal therapeutic catheterization since the device can be applied to patients with a weight of 8 kg and above.

However, there is a limitation to the application of these occlusion plugs since only occlusion plugs with a uniform shape are prepared for various configurations of atrial septal defects and since the occlusion of a defective opening or hole requires use of an occlusion plug twice the size of the defective opening or hole. These devices, therefore, can be applied only to relatively small defective openings or holes present in the central part of the atrioventricular septum. In addition, there is a fear of bad effects due to use of occlusion plugs since there is no data on long-term use of occlusion plugs left in the heart.

The present inventors have already proposed a catheter assembly for intracardiac suture, which is applicable to various configurations of ASD and can percutaneously sew and close ASD, as disclosed in Japanese unexamined patent pplication No. 7-269916. Using this catheter assembly, an trial septal defective opening or hole is closed by piercing the atrial septum with a piercing catheter and transferring the suture with a suture-hooking catheter. However, this catheter assembly is required to transfer the suture with the suture-hooking catheter every time the piercing catheter pierces the atrial septum, and the operation with this catheter assembly is complicated. For this reason, further improvements in this assembly have been desired.

SUMMARY OF THE INVENTION

It is, therefore, an object of the present invention to provide a catheter assembly for intracardiac suture operation, which is suitable for various configurations of ASD, can be handled with ease and can securely sew and close a defective opening or hole.

According to the present invention, the above object is achieved by providing a catheter assembly for intracardiac suture operation comprising:

- a hooking catheter provided with a suture-hooking means at a distal end thereof and with a manipulating element for manipulating the suture-hooking means at a proximal end thereof;
- a piercing catheter having a lumen for movably holding the hooking catheter and provided with a piercing needle at a distal end thereof and with a hemostatic means at a proximal end thereof, the distal portion of said piercing catheter adjacent to the piercing needle being easily bendable;
- a sheath having a lumen for movably holding the piercing catheter and provided with a hemostatic means at a proximal end thereof; and
- a catheter-bending means connected to the piercing needle of the piercing catheter;

wherein the distal portion of said piercing catheter can be easily bent by said catheter-bending means and the bent distal portion can be held in such a state by said catheter bending means.

The suture-hooking means may be composed of two or more super-elastic metal wires (suture-hooking members) formed into an L-shaped hook by inwardly bending the super-elastic metal wires at the distal end portion thereof, and wherein said suture-hooking members extend outwardly at the proximal end portion and bend inwardly at the distal portion so that the components of the L-shaped hook do not intersect each other when the suture-hooking means is extended out of the piercing catheter. Preferably the distal end portion of the suture-hooking members is bent at an angle within the range of 80 and 100 degrees. The piercing catheter and the sheath are provided at the respective proximal ends with a side injection channel for injecting heparinized physiological saline into the suturing site. Generally, the catheter-bending means comprises a wire and a wire take-up means provided at the proximal end of the sheath or the piercing catheter, and wherein the distal end of the wire is fitted, or secured to the proximal end portion of the piercing needle, while the proximal end of the wire passes through the space between the piercing catheter and the sheath and extends out of the proximal end of the sheath, and is connected to the wire take-up means.

The above and other objects and features of the present invention will become clear from the following description of preferred embodiments thereof taken in conjunction with reference to the accompanying drawings which description is given by way of illustration only, and thus is not limitative of the present invention.

DESCRIPTION OF PREFERRED EMBODIMENTS OF THE INVENTION

Figure 1:
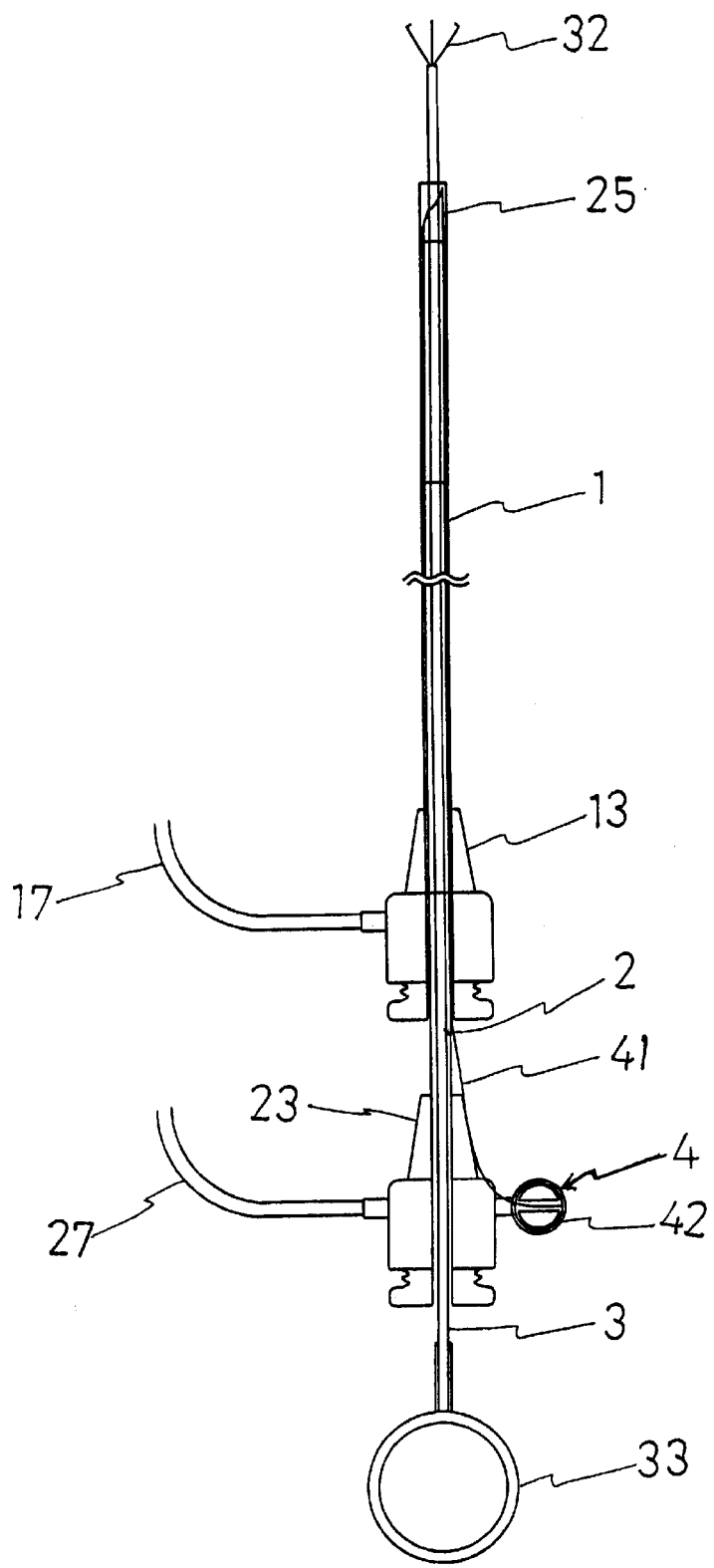
FIG. 1 is a schematic view of a catheter assembly for intracardiac suture according to the present invention.

Preferred embodiments of the invention are described below with reference to the drawings attached hereto.

Figure 2:
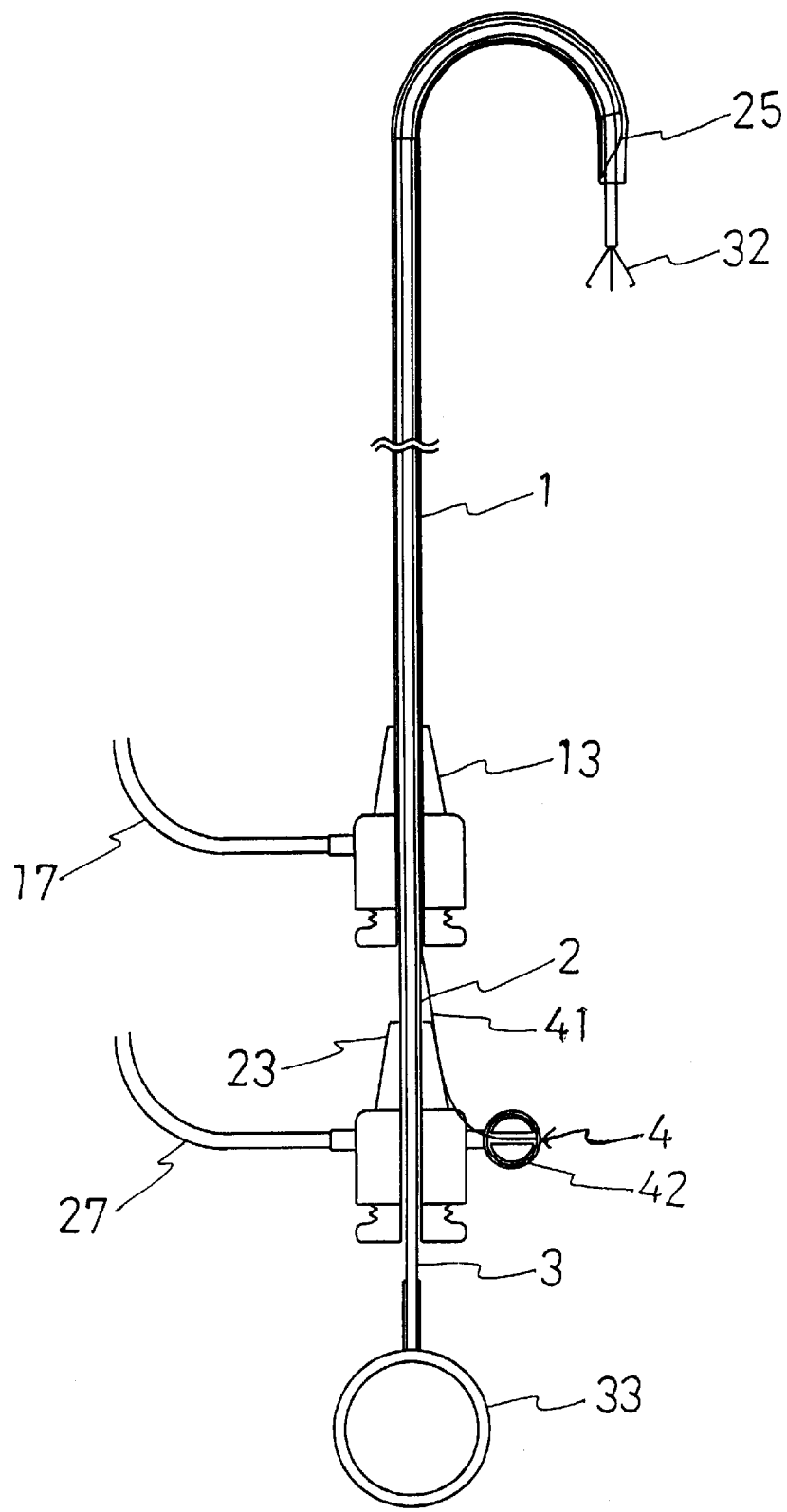
FIG. 2 shows the catheter assembly of FIG. 1, of which the distal end has been bent at 180 degrees.

Referring now to FIGS. 1 to 7, there is shown the catheter assembly for intracardiac suture according to the present invention comprising:

a hooking catheter 3 having a suture-hooking means 32 at a distal end and a manipulating element (grip) 33 at a proximal end;

a piercing catheter 2 having a lumen 21 for movably holding the hooking catheter 3 and a piercing needle 25 at a distal end and a hemostatic valve 24 as a hemostatic means at a proximal end, the distal portion 28 of the piercing catheter adjacent to the piercing needle 25 being easily bendable;

a sheath 1 having a lumen 11 for movably holding the piercing catheter 2 and a hemostatic valve 14 as a hemostatic means at a proximal end; and a catheter-bending means 4 connected to the piercing needle 25 of the piercing catheter 2;

wherein the distal portion 28 of the piercing catheter 2 can be bent by the catheter-bending means 4, as shown in FIG. 2.

Figure 3:
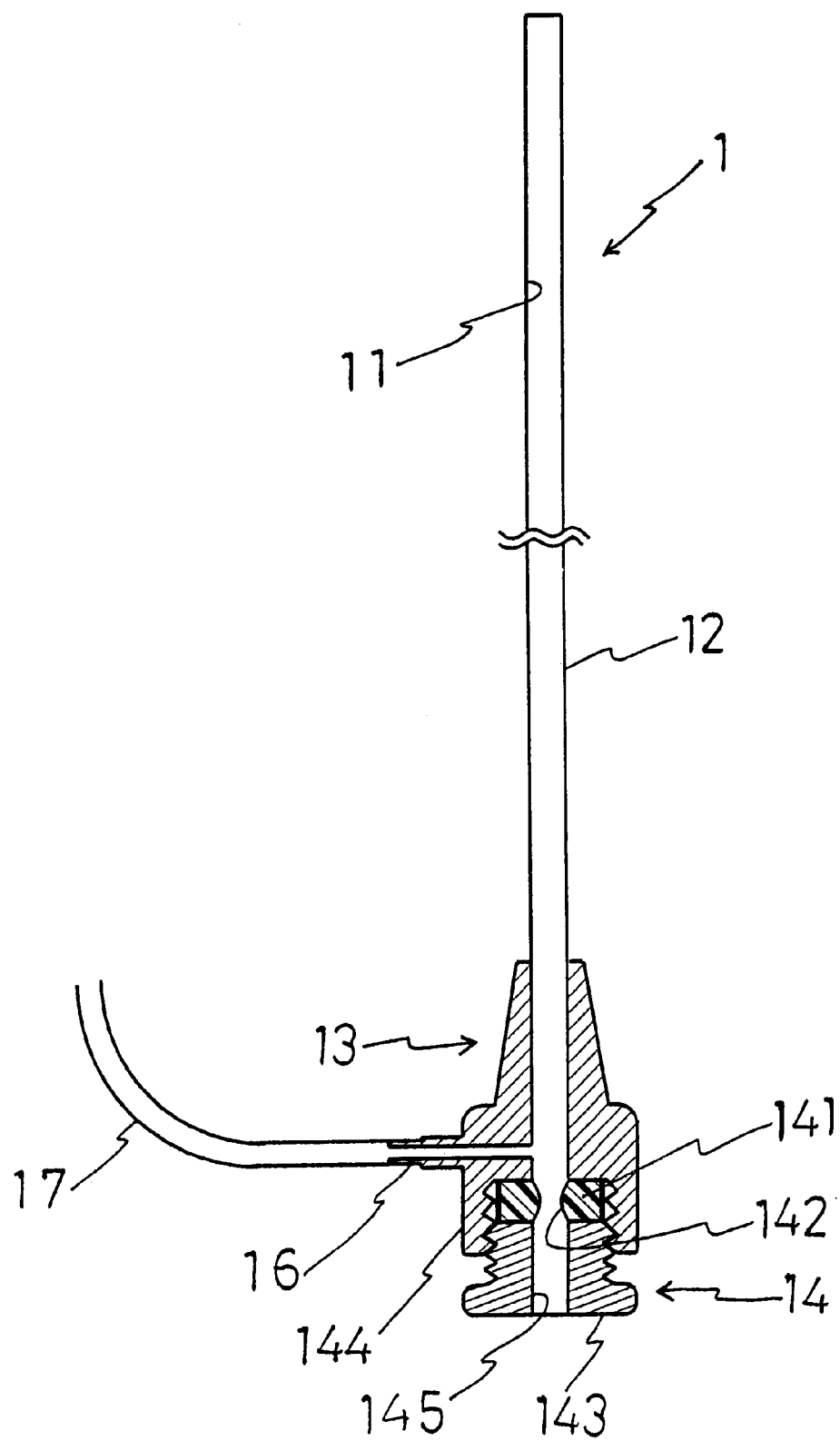
FIG. 3 is a sectional view of the sheath of the catheter assembly of FIG. 1.

As shown in FIG. 3, the sheath 1 is composed of a sleeve 12 with a lumen 11 for free insertion of the piercing catheter 2. The sleeve 12 is provided at its proximal end with a connector 13. The connector 13 has an inlet of the lumen 11, i.e., an insertion hole 145 for the piercing catheter 2, and is provided with the hemostatic means or a hemostatic valve 14 to prevent leakage of blood during a surgical operation. The hemostatic valve 14 is not limited in construction. For example, as shown in FIG. 3, the hemostatic valve 14 is composed of a screw-hole or nut-like means 144 provided in the rear end of the connector 13, and a packing 141 with a central through-hole 142, and a bolt-like member 143 engaged with the screw-hole 144. By driving the bolt-like member 143 into the screw-hole 144, the packing 141 is pressed against the bottom wall of the screw-hole 144 to adjust the inner diameter of the through-hole 142. Further, the connector 13 is generally provided with a side injection channel 16 for injecting heparinized physiological saline into the suturing site to prevent occurrence of blood coagulation during a surgical operation, and the side injection channel 16 is connected to a side injection tube 17. Preferably the distal portion of the sleeve 12 is made bendable to correspond with the bending of the piercing catheter 2.

As the material for the sleeve 12 of the sheath 1, there may be used synthetic resins such as fluororesins (e.g., polytetrafluoroethylene), polypropylene, polyethylene, polyamide, polyethylene terephthalate, polyurethane and the like, and also meshed or coiled stainless steel (e.g., SUS 304). The connector 13 is generally made from a synthetic resin that includes polypropylene, ABS (acrylonitrile-butadienestyrene) resins, polyvinyl chloride, polyethylene, polyethylene terephthalate and the like, or even from a metal such as stainless steel, brass or the like. The packing 141 of the hemostatic valve 14 may be made from a material with rubber elasticity, for example, synthetic rubber, such as silicone rubber or isoprene rubber, or natural rubber. As the material for the bolt-like means, there may be used synthetic resins such as polycarbonate, ABS resin and the like.

Figure 4:
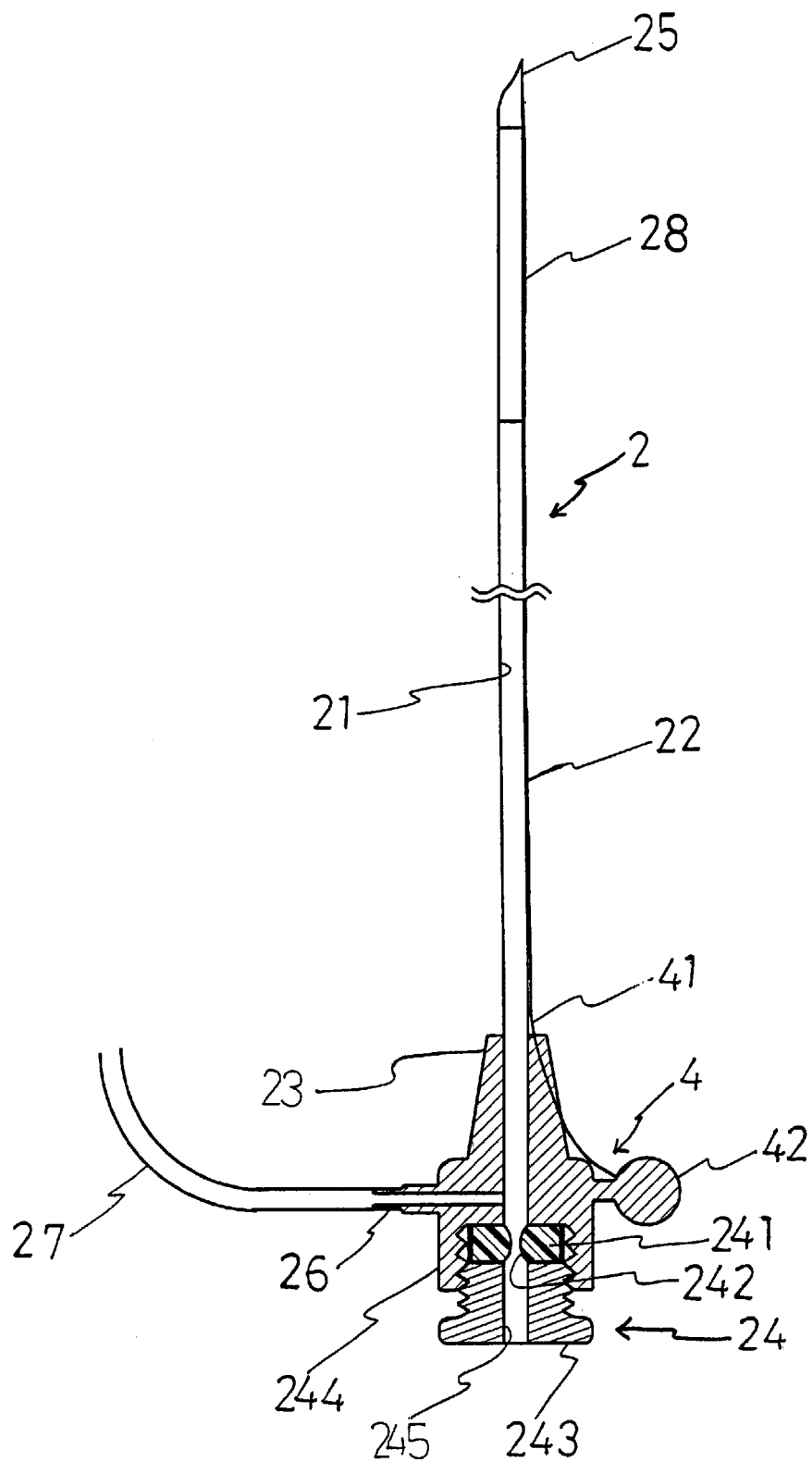
FIG. 4 is a sectional view of the piercing catheter of the catheter assembly of FIG. 1.

As shown in FIG. 4, the piercing catheter 2 is composed of a sleeve 22 having a lumen 21 for movably holding the hodking catheter 3 and is provided at a distal end with a piercing needle 25 and at a proximal end with a connector 23. The connector 23 has an inlet of the lumen 21, i.e., a insertion hole 245 for the hooking catheter 3, and is provided with a hemostatic means (or a hemostatic valve) 24 to prevent leakage of blood during a surgical operation. The hemostatic valve 24 has the same structure as that of the hemostatic valve 14 of the sheath 1, and is composed of a packing 241, a through-hole 242, a bolt-like member 243 and a nut member 244, as shown in FIG. 4. Further, the connector 23 is generally provided with a side injection channel 26 for injecting heparinized physiological saline into the suturing site to prevent coagulation of blood during a surgical operation. The side injection channel 26 is connected to a side injection tube 27.

The distal portion 28 of the piercing catheter 2 adjacent to the piercing needle 25 is easily bendable, and the catheter-bending means 4 is connected to the piercing needle 25. The catheter-bending means 4 can easily bend the bendable distal portion 28 of the piercing catheter 2, and the bent distal portion can be held in such a state by said catheter bending means. As the catheter-bending means 4, there may be used, for example, a wire 41 and a wire take-up device 42. The distal end of the wire 41 is fitted to the proximal end portion of the piercing needle 25, while the proximal end of the wire passes through the space between the piercing catheter 2 and the sheath 1 to be exposed outside of the proximal end of the sheath 1, and is connected to the wire take-up device 42. The wire take-up device 42 may be fitted to either the connector 13 of the sheath 1 or the connector 23 of the piercing catheter 2. Preferably, the wire take-up means 42 is provided with a locking member which can be locked every time the wire is wound up, so that the wire 41 cannot go back in case the operator releases his hold. However, since the suturing operation is repeated, the locking member must be an unlockable one.

Figure 6:
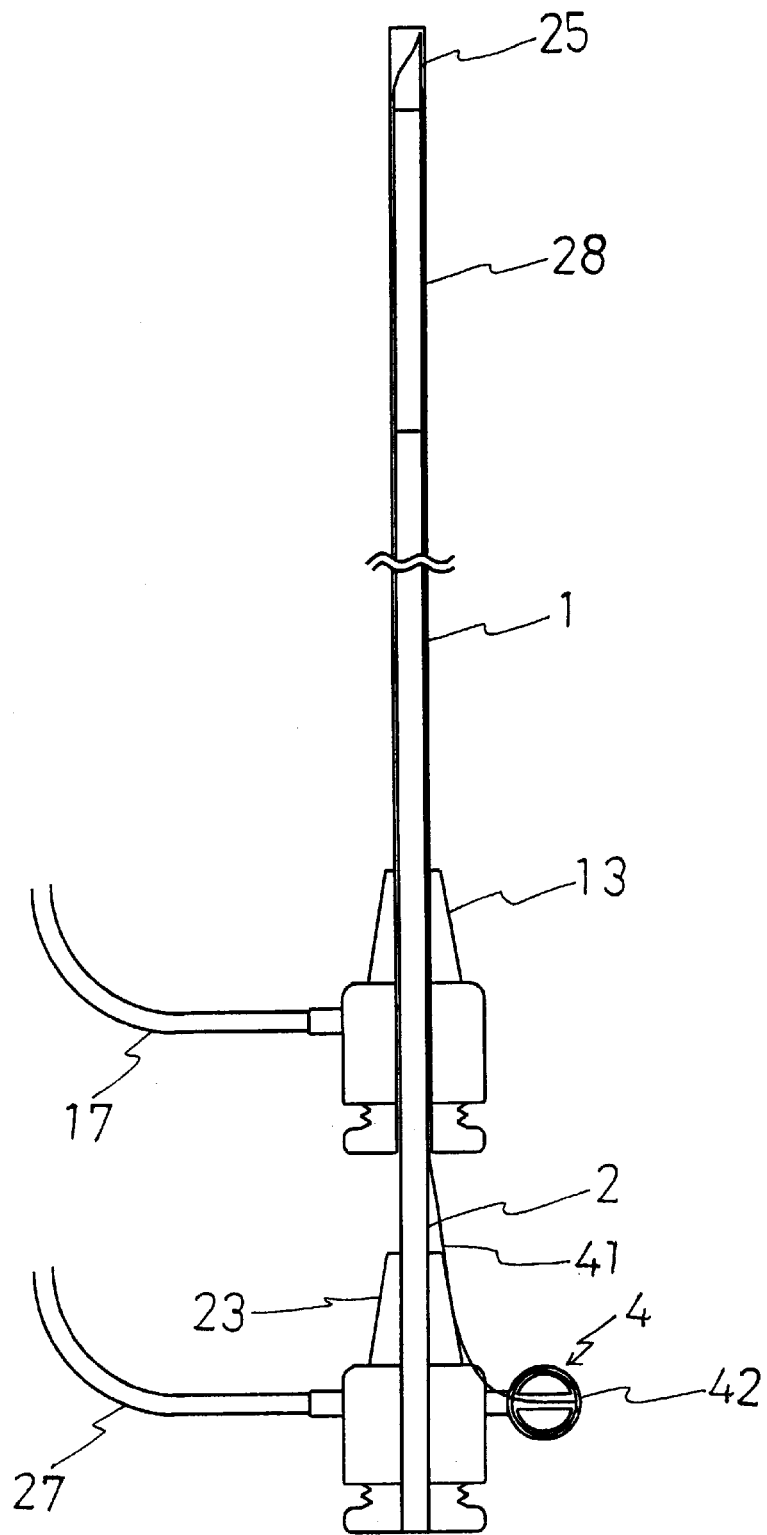
FIG. 6 is a schematic view of the combination of the piercing catheter and the sheath of the catheter assembly of FIG. 1.
Figure 7:
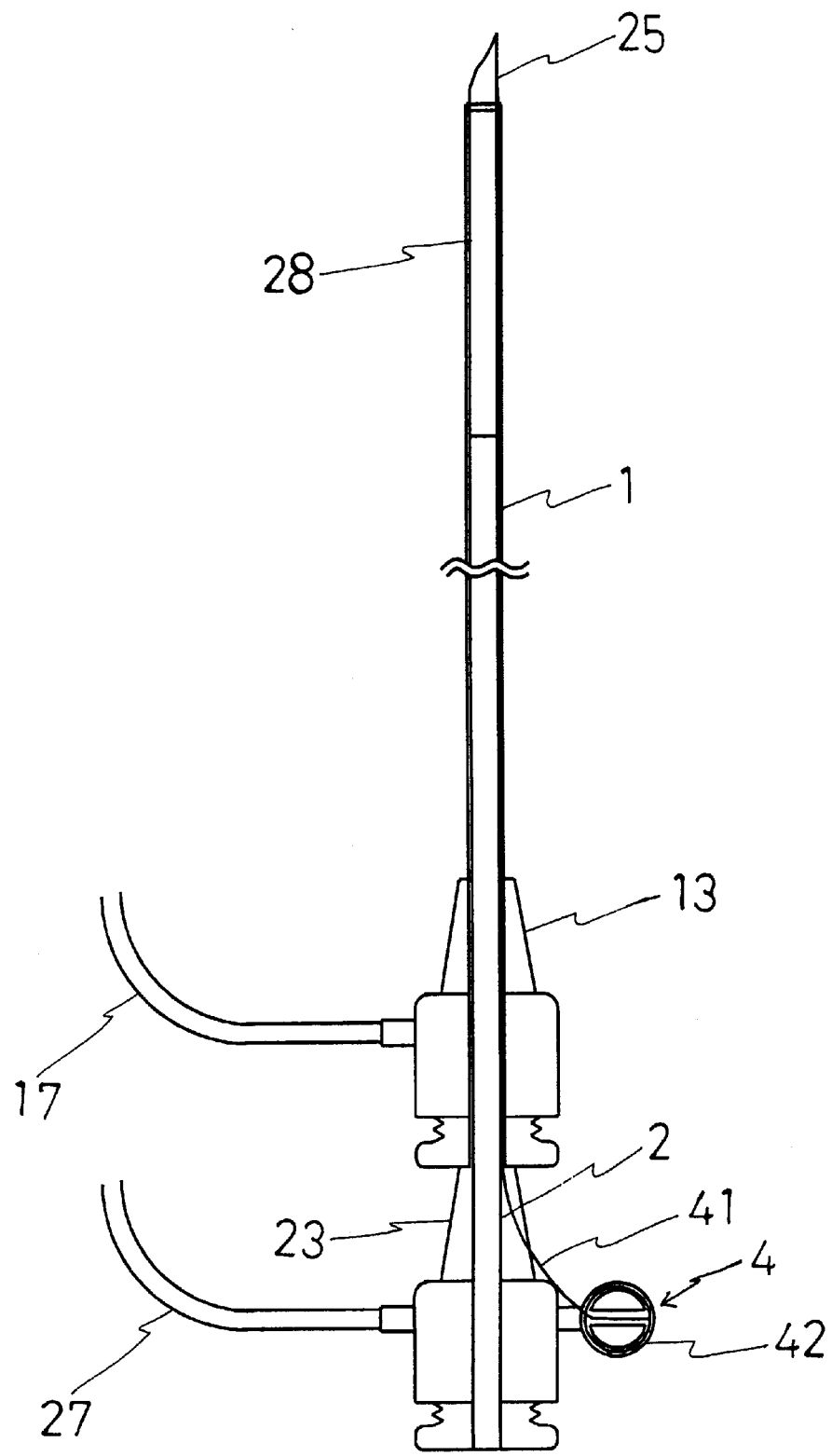
FIG. 7 is a schematic view of the combination of FIG. 6, in which a predetermined length of the piercing needle of the piercing catheter has been stuck out of the sheath.
Figure 8:
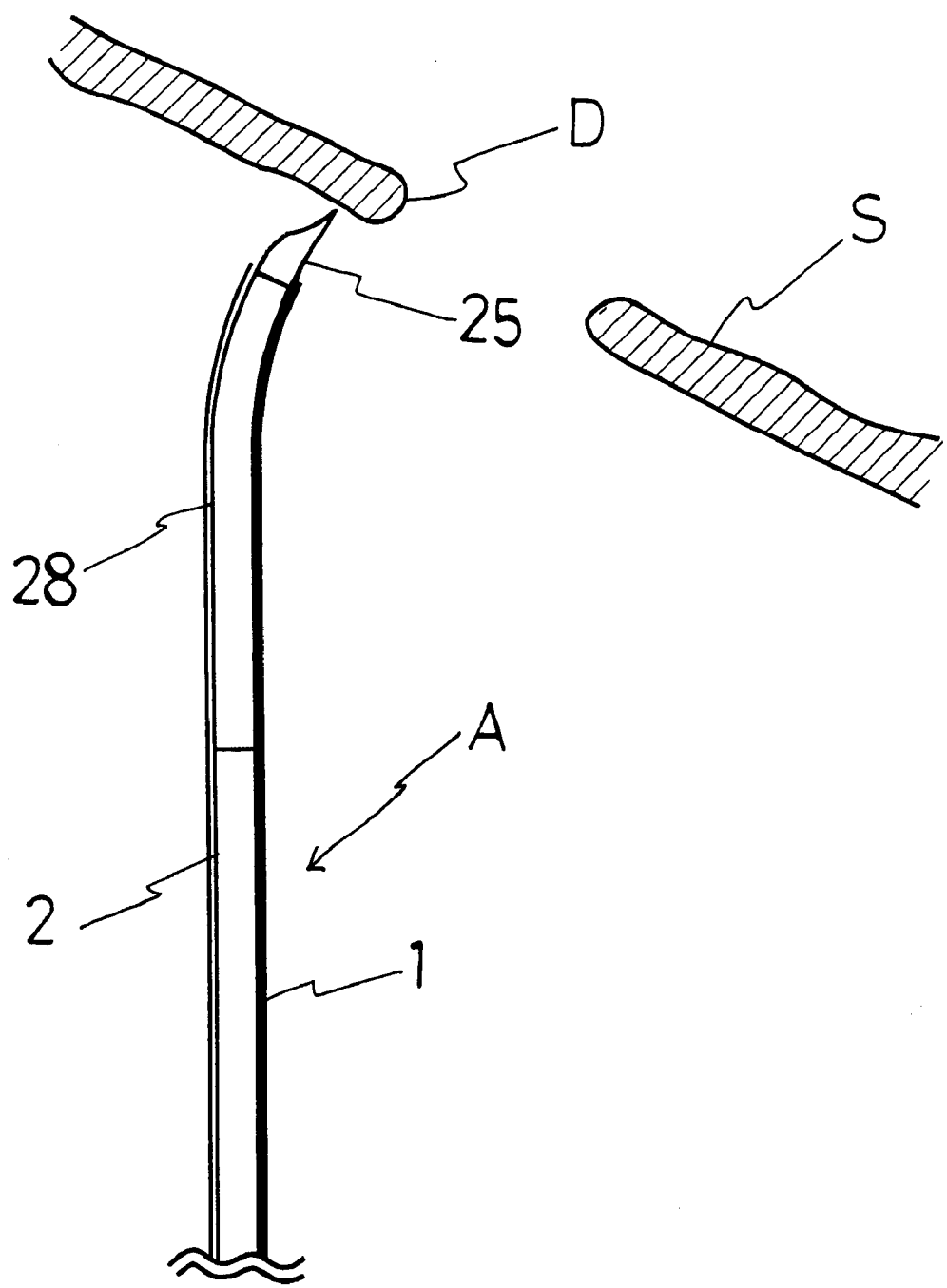
FIGS. 8 to 12 are explanatory views illustrating an intracardiac suture with the catheter assembly of the invention.

As shown in FIG. 6, the piercing catheter 2 is generally inserted in the lumen 11 of the sheath 1. The piercing catheter 2 is slid forward in the lumen 11 of the sheath 1, and when the top of the connector 23 of the piercing catheter 2 is brought into contact with the bottom of the connector 13 of the sheath 1, a predetermined length of the piercing needle 25 extends out of the sheath 1, as shown in FIG. 7. The length the piercing needle 25 extends out of the sheath 1 is preferably such that the edge of the piercing needle 25 is fully extended.

Regarding the material of the piercing catheter 2, the sleeve 22 is preferably made of meshed or coiled stainless steel, while the connector 23 is generally made from a synthetic resin such as polypropylene, ABS resin, polyvinyl chloride, polyethylene and polyethylene terephthalate, or a metal such as stainless steel, brass or the like. Preferably, the bendable distal portion 28 may be made from a synthetic resin such as nylon, polyethylene, polyethylene terephthalate or the like, or a meshed or coiled stainless steel. The piercing needle 25 may be generally made of stainless steel such as SUS 304or the like.

Figure 5:
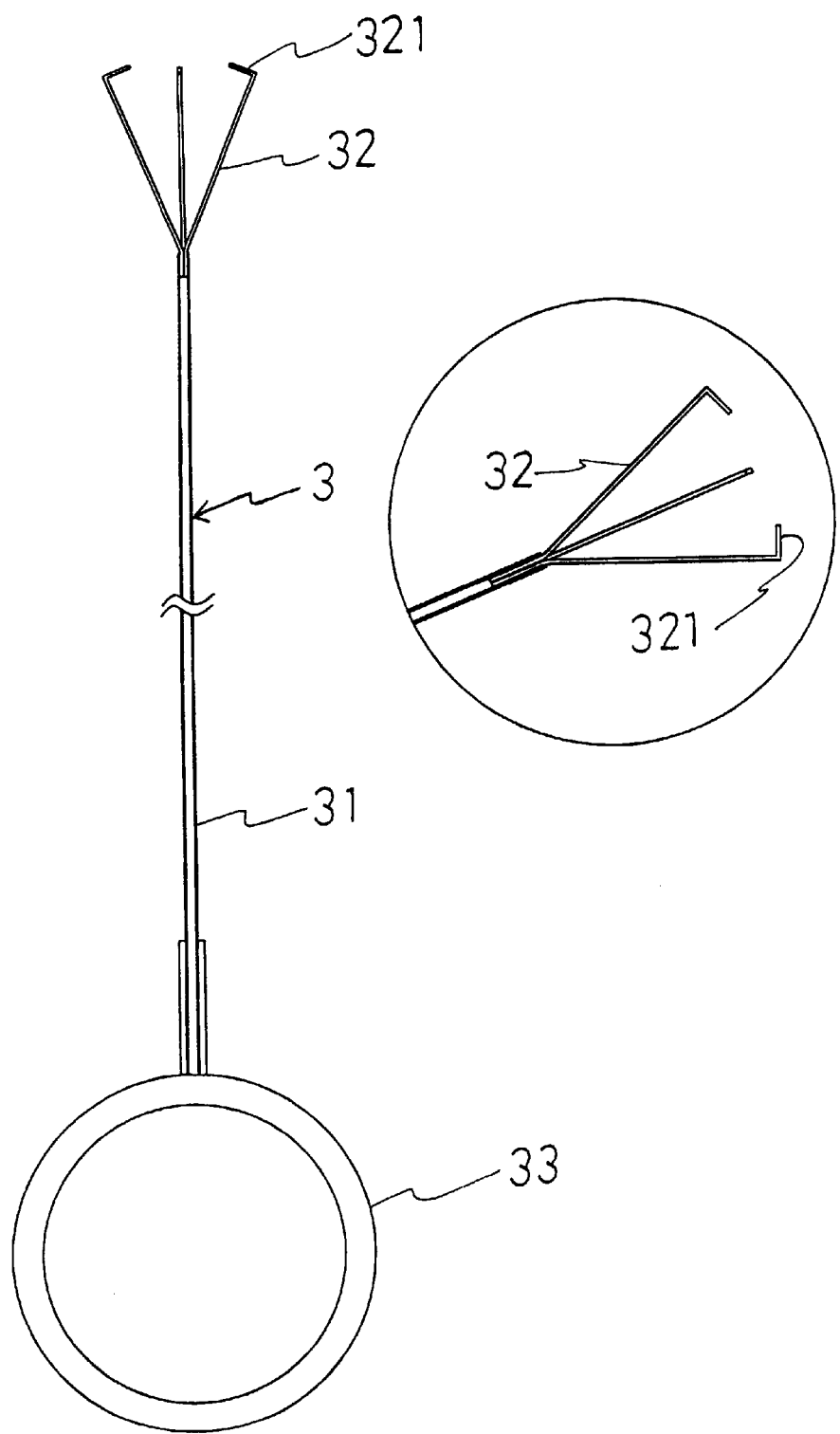
FIG. 5 is a sectional view of the hooking catheter of the catheter assembly of FIG. 1.

As shown in FIG. 5, the hooking catheter 3 is provided with a shaft 31 having a suture-hooking means 32 at a distal end, and a finger ring 33 provided on the proximal end of the shaft 31 as the manipulating element. The finger ring 33 may be made from a synthetic resin or a metal. The shaft 31 is generally made of a coiled metal wire such as stainless steel (e.g., SUS 304), tungsten, titanium or the like. Generally, the suture-hooking means 32 provided at the distal end of the shaft 31 is composed of a plurality of (generally, 3 or 4) hooking members made from wires of stainless steel (e.g., SUS 304) or a super-elastic metal (e.g., alloys of titanium-nickel, alloys containing copper and zinc, or the like). The hooking members are fixed at their proximal ends to the distal end of the shaft 31, extend outwardly and longitudinally from the shaft 31, and are bent at their distal end portions inwardly at an angle of about 90 degrees, preferably, in the range of 80to 100 degrees to form L-shaped hooks 321. The proximal ends of the hooking members are so formed that the suture-hooking means 32 is able to expand outwardly at an angle of 15 to 30 degrees when it is extended out of the piercing catheter 2. Because of such an arrangement, when the suture-hooking means 32 is put out of the piercing catheter 2, as in FIG. 1, the hooking members do not intersect each other and can hold a suture at their hooks 321.

Using the thus-constructed catheter assembly for intracardiac suture according to the present invention, ASD atrioseptopexy is carried out in the following manner. This atrioseptopexy will be explained below, making reference to FIGS. 8 to 12.

Figure 9:
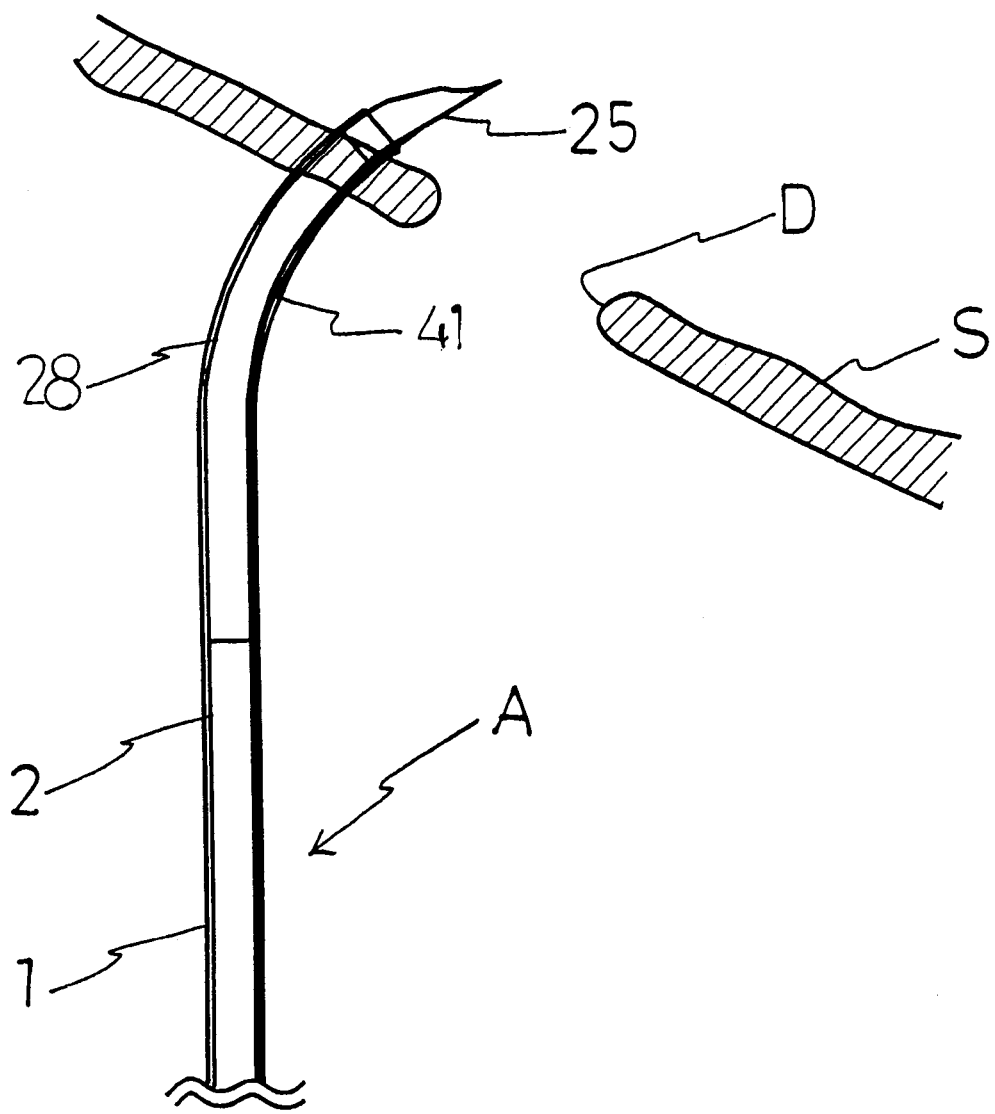
Figure 10:
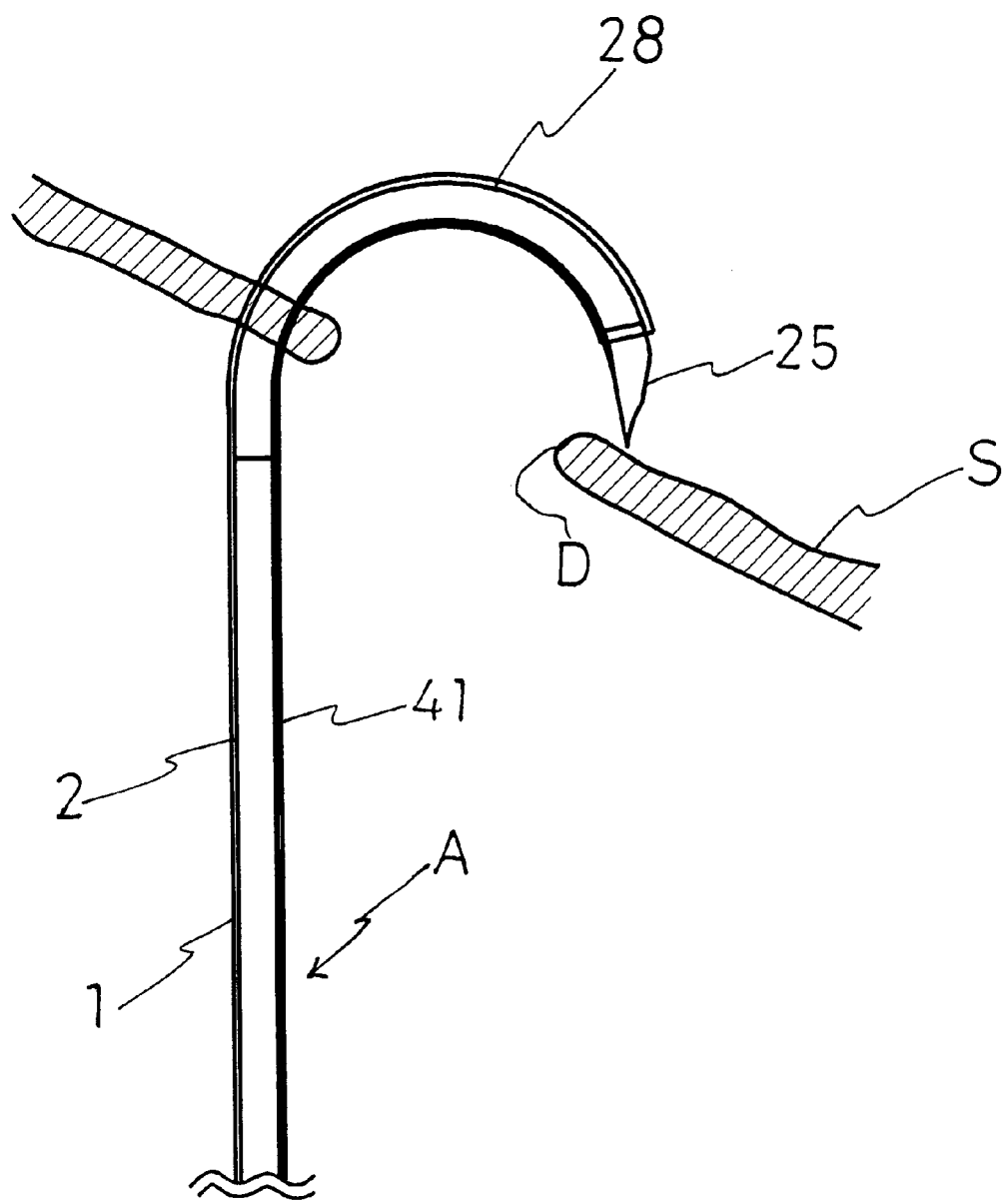
Figure 11:
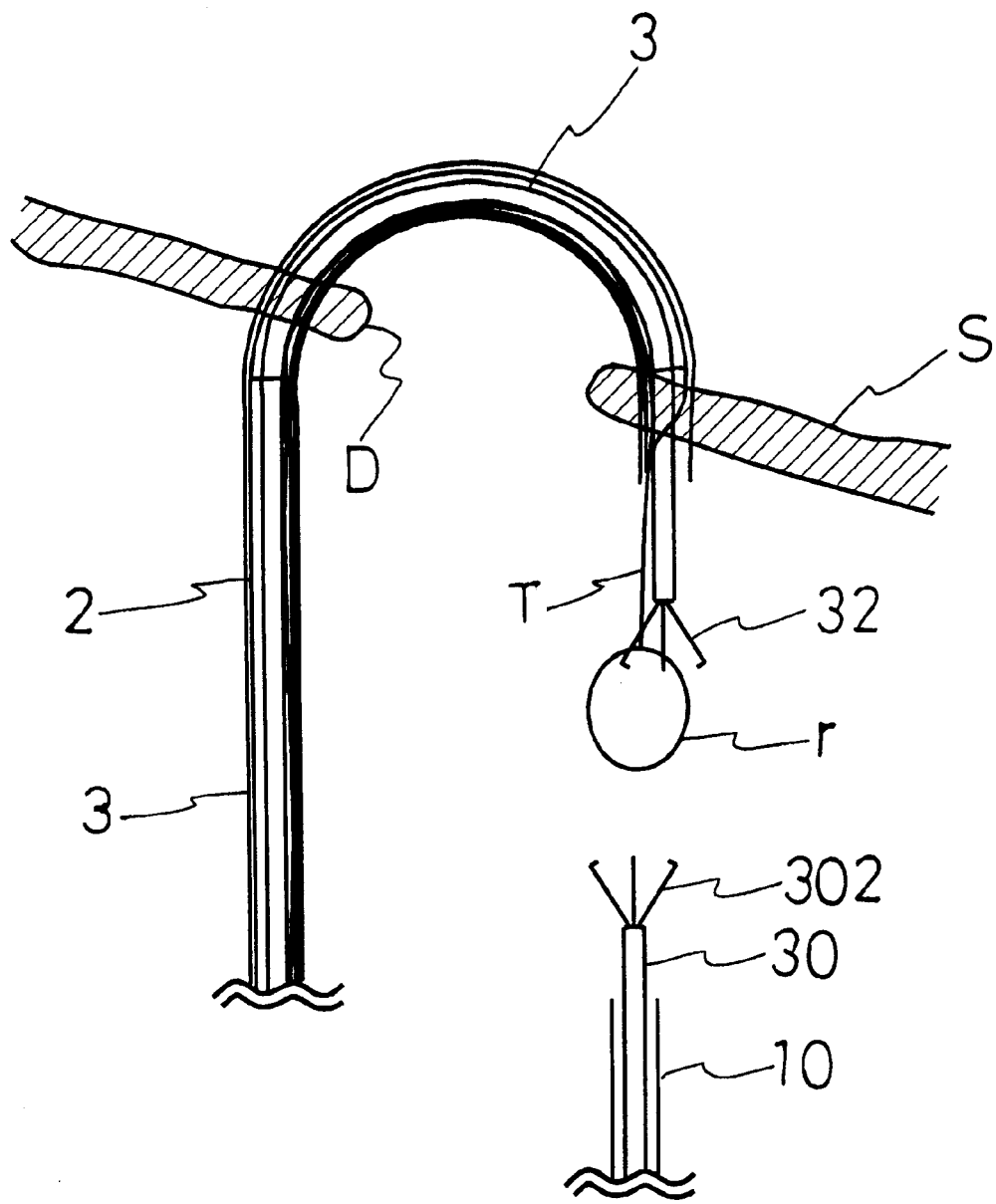
Figure 12:
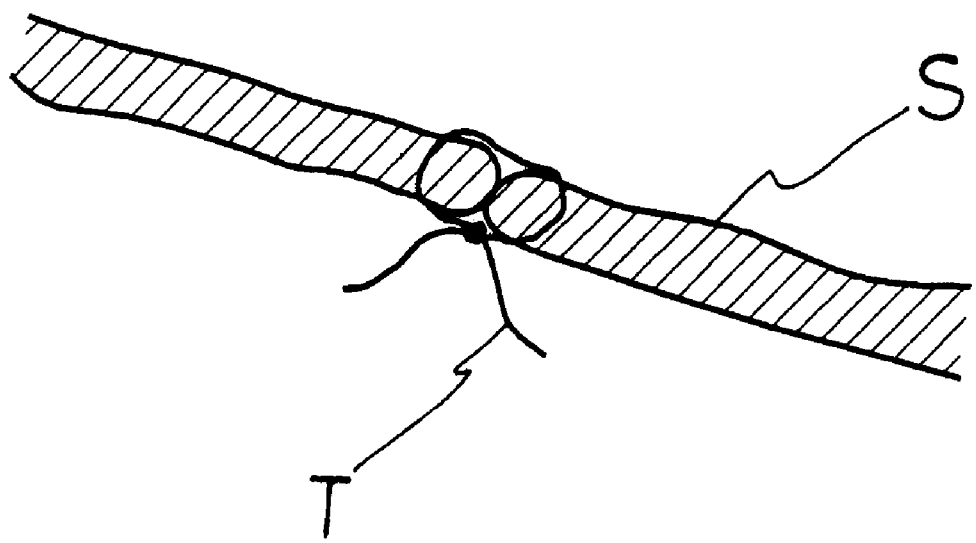

Firstly, the catheter assembly "A" comprises the sheath 1 and the piercing catheter 2, which has been set in the state shown in FIG. 6 and in which both the top of the sheath 1 and the top of the piercing needle 25 of the piercing catheter 2 are in the same position. The catheter assembly is maneuvered into a sheath (not shown), which has been previously maneuvered into the right atrium of a patient's heart through a femoral vein of the right leg, and is introduced into the right atrium of the patient's heart. After the distal end portion of the catheter assembly "A" has been introduced into the right atrium, the wire 41 is wound, if desired, by manipulating the wire take-up device 42 of the catheter-bending means so that the distal portion of the assembly "A" is suitably bent (in such a manner that the piercing needle 25 may be perpendicular to the interatrial septum). Thereafter the piercing needle 25 is put out of the tip of the sheath 1, as in FIG. 8, by pushing the connector 23 of the piercing catheter 2 forward by one hand, while holding the sheath 1 by the other hand. Next, the catheter assembly "A" is pushed to puncture the interatrial septum "S" with the piercing needle 25, whereby the distal end portion of the catheter assembly "A" is introduced into the left atrium, as shown in FIG. 9. Next, the catheter assembly "A" is further pushed until the major part of the bendable distal portion 28 of the piercing catheter 2 is positioned into the left atrium, and the wire 41 is wound by manipulating the wire take-up device 42 of the catheter-bending means 4 while holding the piercing catheter 2 by hand, whereby the catheter assembly "A" is bent as shown in FIG. 10. Since the wire take-up device 42 is locked by a locking member every time the wire 41 is wound up, the catheter assembly "A" is kept bent.

While the catheter assembly "A" is kept bent, the catheter assembly "A" is pulled, whereby the piercing needle pierces through the interatrial septum "S", and the distal portion of the catheter assembly "A" is introduced from the left atrium into the right atrium. Then, the piercing catheter 2 is pulled to position the piercing needle 25 in the sheath 1, and thereafter hooking catheter 3 having a suture thread "T" as previously set therein is inserted into the catheter assembly "A" through the insertion hole 245 of the piercing catheter 2, and the suture-hooking means 32 of the hooking catheter 3 is positioned out of the assembly "A". In this condition, the suture thread "T" is introduced into the right atrium, and the loop "r" of the suture thread "T" is positioned out of the piercing catheter 2. Next, another hooking catheter 30 with no suture thread "T" is introduced into the right atrium, as in FIG. 11, to take up the suture thread "T" that has been brought into the right atrium in the above operation. To introduce the hooking catheter 30 into the right atrium, the hooking catheter 30 is inserted into the sheath 10 which has been maneuvered previously into the right atrium through the same or opposite femoral vein as for the assembly "A".Next, the suture thread "T" is hooked by the suture-hooking means 302 of the hooking catheter 30 so that the hooking catheter 30 receives the suture thread "T" from the hooking catheter 3 and brings the suture thread "T" out of the sheath 10. In that manner, one stitch is put in the interatrial septum across the defect aperture "D". Next, the suture thread "T" is ligated and cut by a suture-ligating tool (not shown), whereby the ASD atrioseptopexy is finished, as in FIG. 12. In case of two or more stitches being required, the same process as above is repeated.

As mentioned above, use of the catheter assembly for intracardiac suture of the invention makes it possible to close the affected part by direct suture, so that it can be applied to any form of atrial septal defect. Further, it is possible to securely close the atrial septal defect. An intracardiac suture by the catheter assembly of the invention is free from any danger since it does not leave any foreign material except the suture and since there is no separation or problems of the devices which may occur with use of the conventional ASD devices.

Although the present invention has been fully described in connection with preferred embodiments thereof with reference to the accompanying drawings, it is to be noted that various changes and modifications will be apparent to those skilled in the art. Such changes and modifications are to be understood as included within the scope of the invention as defined by the appended claims.

What is claimed is:

1. A catheter assembly for intracardiac suture, comprising:

a hooking catheter having a distal end and a proximal end and provided with a suture-hooking means at the distal end thereof and with a manipulating element for manipulating the suture-hooking means at the proximal end thereof;

a piercing catheter having a distal end and a proximal end and having a lumen for movably holding the hooking catheter and provided with a piercing needle at the distal end thereof and with a hemostatic means at the proximal end thereof, a distal end portion of said piercing catheter adjacent to the piercing needle being easily bendable;

a sheath having a distal end and a proximal end and having a lumen for movably holding the piercing catheter and provided with a hemostatic means at the proximal end thereof; and a catheter-bending means connected to the piercing needle of the piercing catheter;

wherein the distal end portion of said piercing catheter can be easily bent by said catheter-bending means and the bent distal end portion can be held in a bent state by said catheter bending means.

2. The catheter assembly according to claim 1, wherein said suture-hooking means comprises two or more suture-hooking members, each member being a super-elastic metal wire formed into an L-shaped hook by bending said super-elastic metal wire at a distal end portion thereof, and wherein said suture-hooking members extend outwardly at a proximal end portion and are bent inwardly at the distal end portion so that the distal portions do not intersect each other when the suture-hooking means is extended out of the piercing catheter.

3. The catheter assembly according to claim 2, wherein the distal end portion of each suture-hooking member is bent at an angle within a range of 80 and 100 degrees.

4. The catheter assembly according to claim 1, wherein the piercing catheter and the sheath are provided at the respective proximal ends thereof with a side injection channel for injecting heparinized physiological saline into a suturing site.

5. The catheter assembly according to claim 2, wherein the piercing catheter and the sheath are provided at the respective proximal ends thereof with a side injection channel for injecting heparinized physiological saline into a suturing site.

6. The catheter assembly according to claim 3, wherein the piercing catheter and the sheath are provided at the respective proximal ends thereof with a side injection channel for injecting heparinized physiological saline into a suturing site.

7. The catheter assembly according to claim 1, in which the catheter-bending means comprises a wire and a wire take-up means provided at the proximal end of the sheath or the piercing catheter, and wherein the distal end of the wire is fitted to a proximal end portion of the piercing needle, while a proximal end of the wire passes through the space between the piercing catheter and the sheath and extends out of the proximal end of the sheath, and is connected to the wire take-up means.

8. The catheter assembly according to claim 2, in which the catheter-bending means comprises a wire and a wire take-up means provided at the proximal end of the sheath or the piercing catheter, and wherein the distal end of the wire is fitted to a proximal end portion of the piercing needle, while a proximal end of the wire passes through the space between the piercing catheter and the sheath and extends out of the proximal end of the sheath, and is connected to the wire take-up means.

9. The catheter assembly according to claim 3, in which the catheter-bending means comprises a wire and a wire take-up means provided at the proximal end of the sheath or the piercing catheter, and wherein the distal end of the wire is fitted to a proximal end portion of the piercing needle, while a proximal end of the wire passes through the space between the piercing catheter and the sheath and extends out of the proximal end of the sheath, and is connected to the wire take-up means.

10. The catheter assembly according to claim 4, in which the catheter-bending means comprises a wire and a wire take-up means provided at the proximal end of the sheath or the piercing catheter, and wherein the distal end of the wire is fitted to a proximal end portion of the piercing needle, while a proximal end of the wire passes through the space between the piercing catheter and the sheath and extends out of the proximal end of the sheath, and is connected to the wire take-up means.

11. The catheter assembly according to claim 5, in which the catheter-bending means comprises a wire and a wire take-up means provided at the proximal end of the sheath or the piercing catheter, and wherein the distal end of the wire is fitted to a proximal end portion of the piercing needle, while a proximal end of the wire passes through the space between the piercing catheter and the sheath and extends out of the proximal end of the sheath, and is connected to the wire take-up means.

12. The catheter assembly according to claim 6, in which the catheter-bending means comprises a wire and a wire take-up means provided at the proximal end of the sheath or the piercing catheter, and wherein the distal end of the wire is fitted to a proximal end portion of the piercing needle, while a proximal end of the wire passes through the space between the piercing catheter and the sheath and extends out of the proximal end of the sheath, and is connected to the wire take-up means.

* * * * *